United States Patent [19]
Kieval et al.

[11] Patent Number: 5,507,782
[45] Date of Patent: Apr. 16, 1996

[54] METHOD AND APPARATUS FOR DUAL CHAMBER CARDIAC PACING

[75] Inventors: Robert S. Kieval, Golden Valley; Michael F. Hess, Minneapolis, both of Minn.

[73] Assignee: Medtronic, Inc., Minneapolis, Minn.

[21] Appl. No.: 214,933

[22] Filed: Mar. 17, 1994

[51] Int. Cl.$^6$ ............................................. A61N 1/36
[52] U.S. Cl. .............................. 607/9; 607/28; 607/30; 607/32
[58] Field of Search ............................................ 607/9, 28

[56] References Cited

U.S. PATENT DOCUMENTS

| | | | |
|---|---|---|---|
| 4,257,423 | 3/1981 | McDonald et al. | 128/419 PG |
| 4,374,382 | 2/1983 | Markowitz | 340/870.01 |
| 4,428,378 | 1/1984 | Anderson et al. | 128/419 PG |
| 4,556,063 | 12/1985 | Tompson et al. | 128/419 PT |
| 5,052,388 | 10/1991 | Sivula et al. | 128/419 PG |
| 5,127,404 | 7/1992 | Wyborny et al. | 128/419P |
| 5,334,220 | 8/1994 | Sholder | 607/9 |
| 5,340,361 | 8/1994 | Sholder | 607/9 |

OTHER PUBLICATIONS

Fananapazir, et al., "Impact of Dual–Chamber Permanent Pacing in Patients With Obstructive Hypertrophic Cardiomyopathy With Symptoms Refractory to Verapamil and β–Adrenergic Blocker Therapy", *Circulation*, 85(6):2149–61, Jun. 1992.

Kappenbarger, J., "The Optimal Patient for Pacemaker–Treatment of Hypertrophic Obstructive Cardiomyopathy (HOCM)," *Pace*, vol. 16, May 1993, Part II, p.–1120.

Jeanrenaud et al. "Effects of Dual–Chamber Pacing in Hypertrophic Obstructive Cardiomyopathy", *The Lance*, 1992; May 30, 1992, vol. 339: 1318–23.

McAreavey, et al, "Altered Cardiac Hemodynamic and Electrical State in Normal Sinus Rhythm After Chronic Dual–Chamber Pacing for Relief of Left Ventricular Outflow Obstruction in Hypertrophic Cardiomyopathy", *American Journal of Cardiology*, 70(6):651–6 Sep. 1, 1992, pp. 651–656.

McDonald, et al., "Permanent Pacing as Treatment for Hypertrophic Cardiomyopathy", *American Journal of Cardiology*, 68(1): 108–110 Jul. 1991, pp. 108–110.

Seidelin et al., "Effects of Dual–Chamber Pacing in Hypertrophic Cardiomyopathy Without Obstruction", *The Lancet*, 340(8815):369–70, Aug. 8, 1992.

Gras, "How to Optimize Pacing Therapy in Patients with Hypertrophic Obstructive Cardiomyopathy: The Importance of AV Delay Programming". *Pace*, vol. 16, May 1993, Part II, p.–1121.

*Primary Examiner*—William E. Kamm
*Assistant Examiner*—Carl H. Layno
*Attorney, Agent, or Firm*—Harold R. Patton; Michael B. Atlass

[57] ABSTRACT

A dual chamber pacemaker and a method of employing the pacemaker to accomplish atrial synchronized ventricular pacing with complete ventricular capture by control of the A-V escape intervals of the pacer. The maximum A-V escape interval effective to accomplish complete ventricular capture is determined and compared to intrinsic A-V conduction time to derive an offset interval. The offset interval is subtracted from the initially measured conduction time to select initial A-V escape interval durations and is subtracted from A-V conduction times measured after implant of the pacemaker to automatically adjust A-V escape interval durations of the pacemaker to maintain complete ventricular capture.

19 Claims, 7 Drawing Sheets

METHOD AND APPARATUS FOR DUAL CHAMBER CARDIAC PACING

BACKGROUND OF THE INVENTION

The present invention relates to cardiac pacing generally and more particularly relates to cardiac pacing modes in which ventricular pacing pulses are delivered synchronized to sensed or paced atrial depolarizations.

The value of dual chamber cardiac pacing in treatment of patients suffering from hypertrophic cardiomyopathy has recently been recognized. The benefits of this therapy are discussed in the articles "Permanent Pacing as Treatment for Hypertrophic Cardiomyopathy" by Kenneth M. McDonald et al., published in the *American Journal of Cardiology*, Vol. 68, Jul. 1, 1991, pp. 108–110, "Impact of Dual Chamber Permanent Pacing in Patients with Obstructive Hypertrophic Cardiomyopathy with Symptoms Refractory to Verapamil and β-Adrenergic Blocker Therapy" by Fananapazir et al., published in *Circulation*, Vol. 8, No. 6, June, 1992, pp. 2149–2161, "Effects of Dual-Chamber pacing in Hypertrophic Obstructive Cardiomyopathy", by Jeanrenaud, et al., published in *The Lancet*, Vol. 33, May 30, 1992, pp. 1318–1323, "Altered Cardiac Hemodynamic and Electrical State in Normal Sinus Rhythm After Chronic Dual-Chamber Pacing for Relief of Left Ventricular Outflow Obstruction in Hypertrophic Cardiomyopathy", by McAreavey et al., published in *American Journal of Cardiology*, 1992, Vol. 70, pp. 651–656, and "Effects of Dual-Chamber Pacing in Hypertrophic Cardiomyopathy Without Obstruction", by Seidelin et al., published in *The Lancet*, 1992, pp. 340–369. In these papers, the value of DDD pacing employing a shortened A-V escape interval is discussed. In particular, the use of an A-V escape interval which is shorter than the patient's intrinsic A-V conduction is specifically recommended, with favorable results being reported so long as the duration of the pacemaker's A-V escape interval is not so short that hemodynamic performance is compromised. Various approaches to selecting the optimal A-V escape interval are discussed in the literature.

It is generally agreed that pre-excitation of the ventricular apex and septum by the ventricular pacing pulse, prior to excitation due to natural conduction between the atrium and ventricle is to be preferred. The abstract "How to Optimize Pacing Therapy in Patients with Hypertrophic Obstructive Cardiomyopathy: The Importance of AV Delay Programming" by Gras, et al., published in *PACE*, May, 1993, Vol. 16, Part II, page 1121 suggests that the longest A-V escape interval which provides complete ventricular capture should be selected. The above-cited article by Fananapazir suggests that the A-V escape interval which allows for maximal pre-excitation of the ventricle by the pacing pulse can be selected by employing the A-V escape interval that produces the widest paced QRS complex duration. The above-cited McDonald article suggests that the A-V escape interval should be set at the longest duration that maintains ventricular capture at maximum exercise levels.

In the abstract "The Optimal Patient for Pacemaker Treatment of Hypertrophic Obstructive Cardiomyopathy (HOCM) by Jeanrenaud et al, published in *PACE*, May, 1933, Vol. 16, Part II, page 1120, it is suggested that in the case of patients who would require an excessively short A-V escape interval in order to accomplish pre-excitation, intrinsic A-V conduction time could be prolonged by means of drugs or ablation techniques.

SUMMARY OF THE INVENTION

The present invention provides a method and apparatus for initializing and controlling the A-V escape intervals of a dual chamber (e.g. DDD or DDDR mode pacemaker), for use in treating patients suffering from hypertrophic obstructive cardiomyopathy. The inventive pacemaker is also believed useful in treating patients having dilated cardiomyopathy, and may also be applicable to patients suffering other forms of heart failure. The invention may be employed in the context of a pacemaker which includes the ability to progressively shorten A-V escape intervals in response to increasing sensed and/or paced atrial rates. However, the invention may also usefully be practiced in the context of a pacemaker employing an A-V escape interval which does not vary with heart rate.

The pacemaker's A-V escape interval is initialized by scanning through the available range of A-V escape intervals during DDD or DDDR mode pacing, and determining the difference between the A-V intrinsic conduction time as measured by the pacemaker and the longest A-V escape interval defined by the pacemaker which provides for complete ventricular capture. In order to accomplish this result, the pacemaker is first adjusted to provide a short A-V escape interval assuring complete ventricular capture. The waveform of the ventricular depolarization (R-wave) following the ventricular pacing pulse is noted, and preferably recorded for comparison with subsequent paced R-waves. The A-V escape interval is then set to a prolonged value, and reduced in duration on a beat by beat basis. The intrinsic A-V conduction time may be measured between sensed atrial depolarizations or delivered atrial pacing pulses and the following spontaneous R-waves during this scan of A-V escape intervals or the intrinsic A-V conduction time may be measured separately. Reduction of the pacemaker's A-V escape interval continues until the waveform of an R-wave following a delivered atrial synchronized ventricular pacing pulse corresponds to the waveform of the R-wave following the initially delivered ventricular pacing pulse, indicative of complete ventricular capture. The pacemaker's A-V escape interval resulting in complete ventricular capture is subtracted from the intrinsic A-V conduction time and is used to define the ventricular sense offset interval (VSO). The initial setting of the pacemaker's A-V escape interval may be set to the intrinsic A-V conduction time minus the ventricular sense offset interval.

The ventricular sense offset interval may also be employed to automatically update and adjust the pacemaker's A-V escape interval, after implant. After each ventricular sensed depolarization falling within the pacemaker's then current A-V escape interval, the pacemaker measures the intrinsic A-V conduction time. The ventricular sense offset is subtracted from the measured A-V conduction time to the pacemaker's new A-V escape interval. As such, the pacemaker actively works to maintain complete ventricular capture, as is desired. The expected result of this adjustment process is that following sensed atrial depolarizations or delivered atrial pacing pulses, ventricular pacing pulses will generally be delivered.

In order to allow the device to respond to an increase in intrinsic A-V conduction time, which would allow for prolongation of the pacemaker's A-V escape interval and presumably improved cardiac function, the pacemaker periodically checks to determine whether the patient's intrinsic conduction time has prolonged. This is accomplished by prolonging the pacemaker's current A-V escape interval by a predetermined increment, and determining whether a sensed ventricular depolarization occurs within the prolonged A-V escape interval. If such a depolarization occurs, the A-V conduction interval is noted and the ventricular sensing offset value is subtracted from it to define the pacemaker's new A-V escape interval.

If a ventricular sensed depolarization does not occur within the prolonged A-V escape interval, the A-V escape interval is repeatedly prolonged until either a ventricular sensed depolarization occurs therein, allowing for redefining of the pacemaker's A-V escape interval or until a maximum A-V escape interval duration is reached.

In the event that a maximum A-V escape interval duration is reached prior to sensing of a ventricular depolarization within the A-V escape interval, further scans of the A-V delay duration may be disabled for a predetermined period of time thereafter and the pacer's A-V escape interval reset to its previous value, in order to prevent excessive and repeated sequences of pacing with gradually increased A-V escape intervals.

In the preferred embodiment of the device, the initialization procedure comprises measuring intrinsic A-V conduction times following both delivered atrial pacing pulses and sensed atrial depolarizations, which measurements are employed to define two differing A-V escape intervals for the pacemaker, following sensed and paced events. The difference between the A-V conduction time following a sensed atrial depolarization and the A-V conduction time following a delivered atrial pacing pulse is referred to as the atrial sense offset (ASO). The pacemaker's A-V escape interval following delivered atrial pacing pulses (PAV) is set equal to the A-V escape interval defined following sensed atrial depolarizations (SAV), plus the atrial sense offset. Thus, in the preferred embodiment, the sensed A-V escape interval (SAV) is equal to the measured intrinsic A-V conduction time following a sensed atrial depolarization (AVC) minus the ventricular sense offset (VSO), while the paced A-V escape interval, (PAV) is equal to the intrinsic A-V conduction time (AVC), minus the ventricular sense offset interval (VSO), plus the atrial sense offset interval (ASO).

DETAILED DESCRIPTION OF A PREFERRED EMBODIMENT

Figure 1:
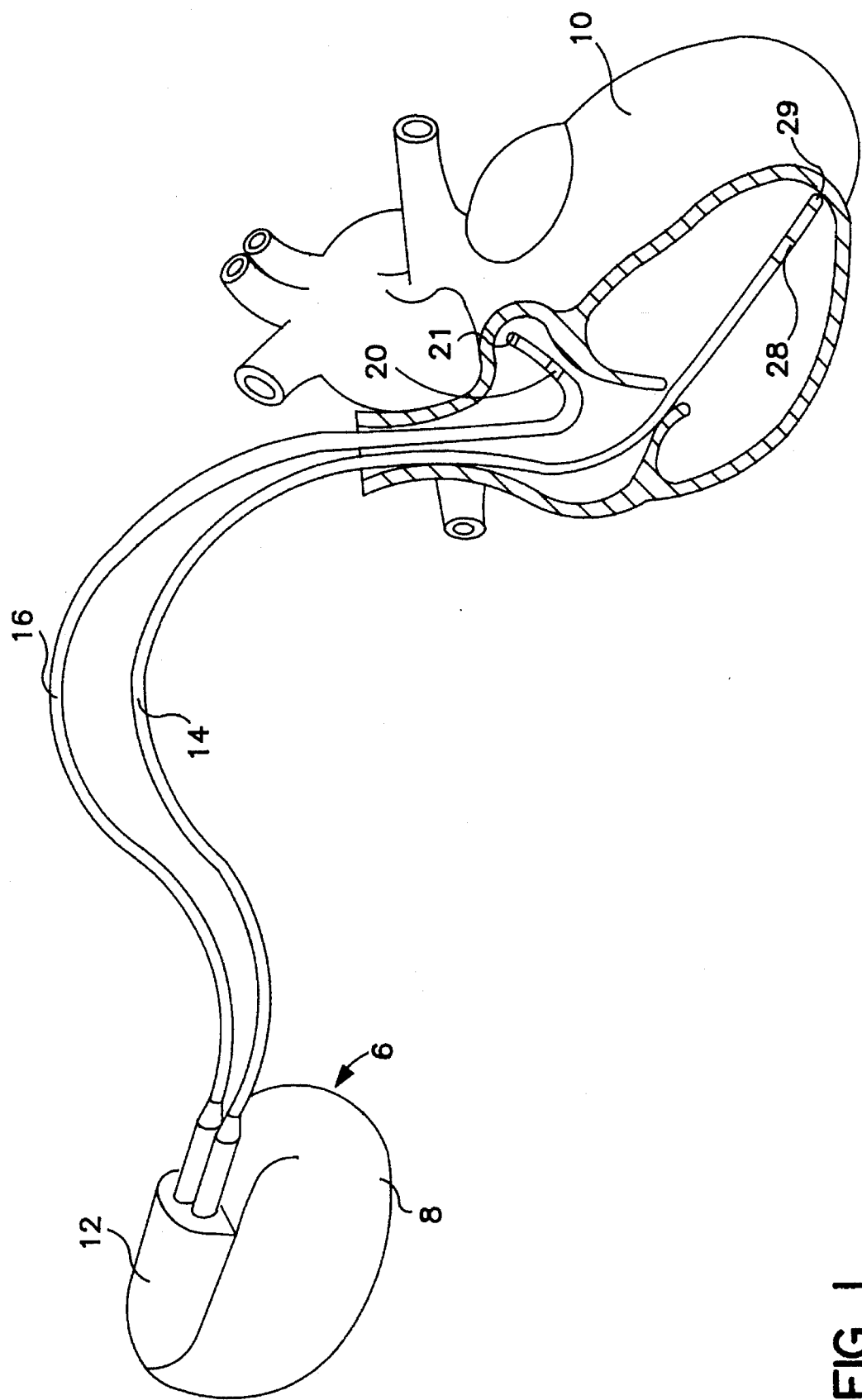
FIG. 1 is an illustration of a dual chamber pacemaker according to the present invention in conjunction with an associated set of cardiac pacing leads, illustrated as located in a cutaway view of a human heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular depolarizations may be accomplished between electrodes 29 and 28 or between either of electrodes 29 and 28 and the housing 8 of the pacemaker 6.

As discussed in the present application, the specific embodiment of the pacemaker 6 disclosed operates in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. While the present invention is believed optimally practiced in a pacemaker operating in DDD pacing mode, in some patients there may also be a benefit to operating the device in VDD or DVI mode, which provide ventricular pacing pulses synchronized to only delivered atrial pacing pulses or synchronized only to sensed atrial depolarizations, respectively, depending upon the specific underlying heart condition of the patient. However, DDD mode is expected to be the mode most widely used to practice the present invention.

Figure 2:
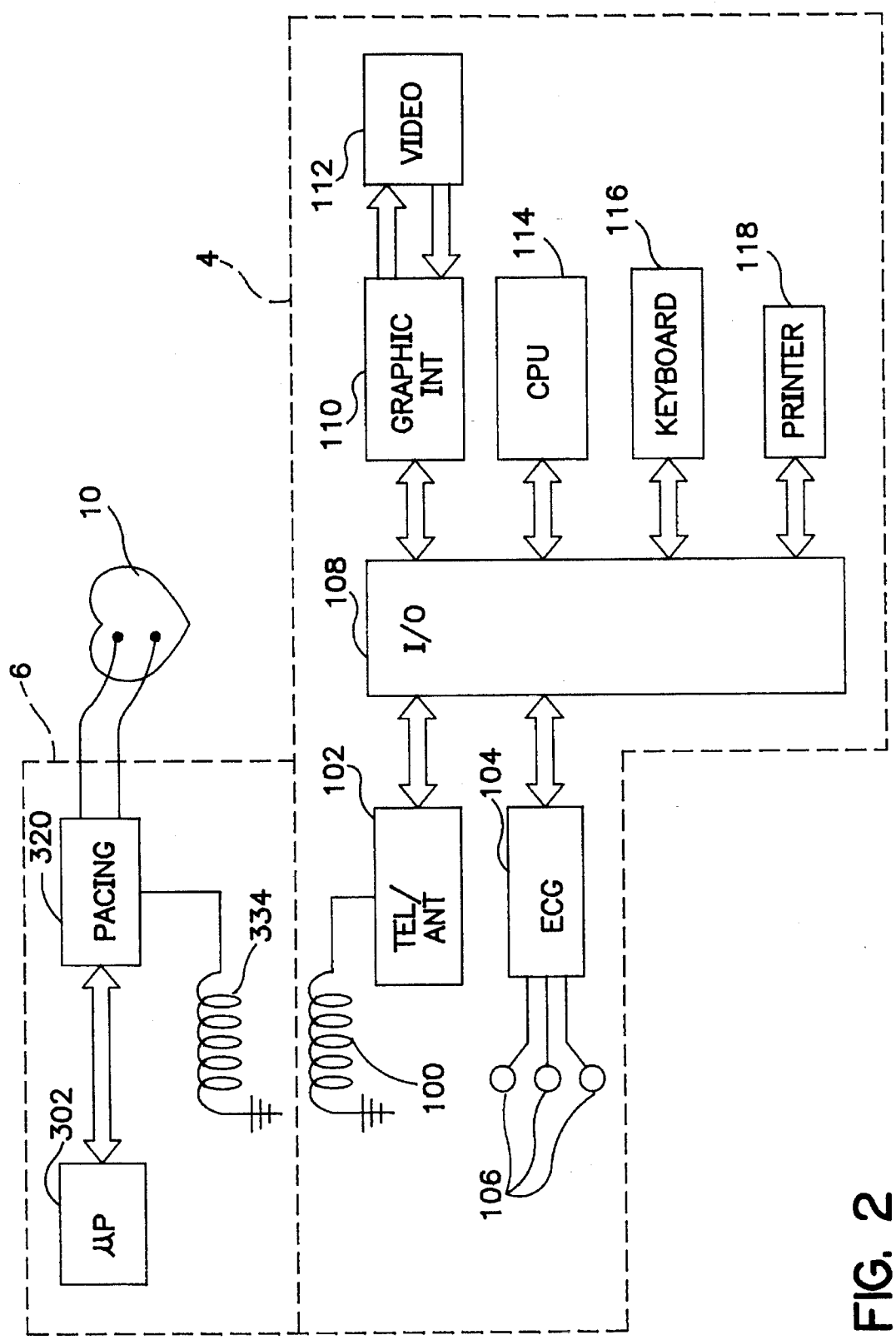
FIG. 2 is a block functional diagram of the dual chamber pacemaker illustrated in FIG. 1 in conjunction with an external programmer/monitoring unit, for use in performing the base A-V escape interval initialization procedure according to the present invention.

FIG. 2 illustrates the pacemaker 6 in block diagram form, coupled to a human heart 10, in conjunction with an external programmer/display apparatus corresponding to those typically employed to program modern, multi-programmable implantable pacemakers. Within the housing of the pacemaker are located the pacing circuitry 320, which includes circuitry performing all of the basic timing, stimulation and sensing functions of a cardiac pacemaker and a microprocessor circuit 302, which controls the timing intervals provided by the pacing circuitry 320. Pacing circuitry 320 also includes a bidirectional telemetry circuit coupled to an antenna 334, allowing transmission of information from external programmer 4 into the pacemaker 6 to modify its parameters and allowing transmission of information from the pacemaker 6 to the external programmer 4, again generally corresponding to telemetry and programming systems presently existing in commercially marketed multi-programmable implantable pacemakers.

The programmer 4 also includes a corresponding antenna 100 coupled to a telemetry/antenna driver circuit 102 which serves to demodulate telemetry signals received from antenna 334 of the pacemaker, and to apply them in parallel or serial digital format to input output (I/O) unit 108, where they in turn may be applied to a video monitor 112 via graphic interface 110, and/or provided to central processing unit 114 and/or printer 118. Microprocessor 114 controls the operation of the programmer/display apparatus, and is responsive to physician entered commands via keyboard 116, for controlling programming signals sent to the pacemaker, as well as for controlling operation of the video display 112 and printer 118. Also illustrated is an ECG interface 104, coupled to three ECG electrodes 106 which are intended to be placed upon the patient's body. ECG interface 104 provides sensed electrograms to input/output device 108, where they in turn may be provided to the video display 112, the central processing unit 114 or the printer 118. The operation of the various portions of the programming/display unit in conjunction with the initialization procedure provided by the present invention is discussed in more detail in conjunction with FIGS. 3–5, below.

Figure 3:
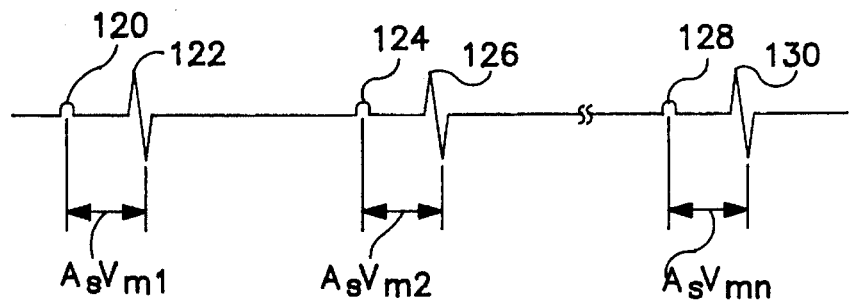
FIG. 3 is a simulated ECG tracing illustrating measurement of intrinsic A-V conduction times following sensed atrial depolarizations, as part of the preferred initialization procedure of the present invention.

FIG. 3 is a simulated ECG strip illustrating measurement of the intervals $A_s V_{m1}$, $A_s V_{m2}$ . . . $A_s V_{mn}$, between the patient's sensed atrial depolarizations 120, 124, 128 and corresponding ventricular depolarizations 122, 126 and 130. Measurements are taken over a series of heart beats, preferably at a resting heart rate. These measured intervals are employed to provide a computed A-V conduction time "AVC", for example by averaging the measured intervals, by selecting the minimum measured interval, or otherwise.

The apparatus of FIG. 2 may be employed in a variety of ways in order to accomplish this measurement function. In one embodiment of the device, the implanted pacemaker directly measures the duration of the intervals ($A_s V_{m1}$, $A_s V_{m2}$ . . . $A_s V_{mn}$), between detection of corresponding sensed atrial and ventricular depolarizations and telemeters these measured intervals to the external programmer, where computation of the average value AVC takes place. Alternatively, calculation of the average could occur internal to the pacemaker. As yet a further alternative, the implanted pacemaker could simply telemeter marker signals in conjunction with each sensed atrial and ventricular event, in the fashion disclosed in U.S. Pat. No. 4,374,382, issued to Markowitz, incorporated herein by reference in its entirety, and the programmer could perform all measurement and calculation functions. In any case, it is anticipated that the physician will initiate the measurement protocol via the keyboard 116, while the patient is in a resting state, which will in turn trigger the microprocessor 114 to activate the pacemaker by telemetry to either measure and record the A-V conduction times or to begin telemetry of marker signals corresponding to the sensed atrial and ventricular events.

Figure 4:
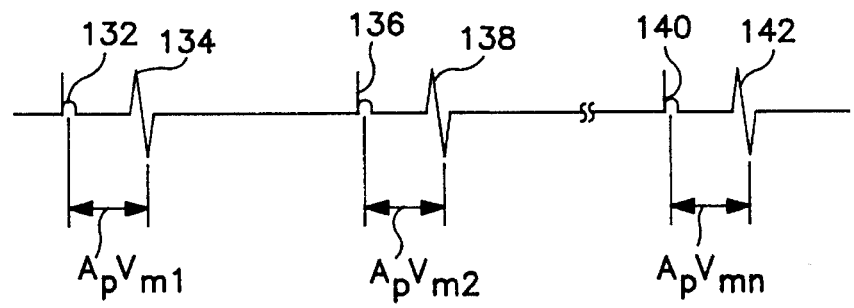
FIG. 4 is a simulated ECG strip illustrating measurement of intrinsic A-V conduction times following delivered atrial pacing pulses as part of the preferred initialization procedure of the present invention.

FIG. 4 illustrates measurement of intervals between delivery of atrial pacing pulses and sensing of the following ventricular depolarizations, by the pacemaker. The patient's sinus rate is measured and the pacer is then programmed to a base pacing interval less that the sinus rate interval (e.g. 85% of sinus rate interval), so that a paced atrial rhythm is produced. In a fashion analogous to that described in conjunction with the FIG. 3, measurements of the intervals $A_p V_{m1}$, $A_p V_{m2}$ . . . $A_p V_{mn}$ are taken, between atrial pacing pulses 132, 136 and 140 and corresponding ventricular depolarizations 134, 138 and 142. As discussed in conjunction with FIG. 3, measurement of the intervals between delivered pacing pulses and sensing of corresponding ventricular depolarizations by the pacemaker may be made either by the pacemaker or the programmer. The values of the measured intervals ($A_p V_{m1}$, $A_p V_{m2}$ . . . $A_p V_{mn}$) are averaged or otherwise used to provide a value corresponding to the time (APVC) between delivery of an atrial pacing pulse and the sensing of a corresponding ventricular depulization by the pacemaker. The value of AVC measured in conjunction with FIG. 3 is subtracted from APVC as determined above, and the difference defines the atrial sense offset interval (ASO) which will be employed to define the difference between the pacemaker's A-V escape interval following sensed atrial events (SAV) and the pacemaker's A-V escape interval following paced atrial events (PAV). PAV will be set equal to SAV plus ASO. It should be noted that in some instances it is possible that the value of ASO may be negative, although as illustrated in the drawings herein it is shown as having a positive value.

Figure 5:
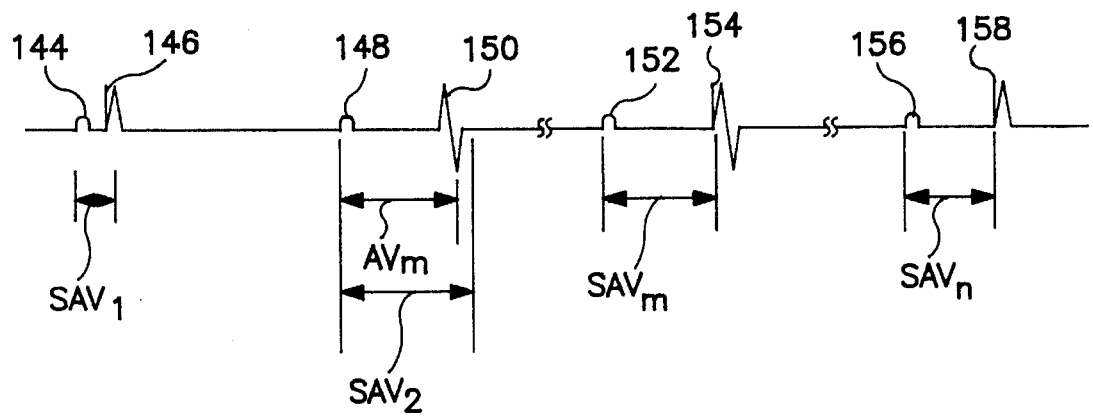
FIG. 5 is a simulated ECG strip illustrating measurement of the ventricular sense offset value, as part of the initialization procedure performed according to the present invention.

FIG. 5 illustrates a method for determining the ventricular sense offset (VSO) associated with the initialization process of the present invention. This process is begun by placing the pacer in DDD or DDDR mode, and a short A-V escape interval ($SAV_1$) is specified, separating sensed depolarization 144 from ventricular pacing pulse 146. The value of $SAV_1$ is set to be short enough to assure complete ventricular capture, for example about 100 milliseconds. Preferably, ECG electrodes 106 are mounted to the patient to allow sensing of a surface electrocardiogram, which is provided to the graphic interface 110 and video display 112 and/or central processing unit 114 and/or printer 118, so that the waveform of the R-wave following pacing pulse 146 may be stored for later reference. Storage of the waveform may be as simple as a paper printout of the ECG provided by printer 118, or may involve digital electronic storage of the waveform either by central processing unit 114 or by the graphic interface 110. Alternatively, the doctor may simply observe and remember the waveform of the depolarization following pacing pulse 146.

The A-V escape interval of the pacemaker is then prolonged substantially to a value (SAV2), e.g. 400 ms, following the next sensed atrial depolarization 148. As illustrated, a sensed ventricular depolarization 150 occurs within this interval. Optionally, the interval between atrial depolarization 148 and sensed depolarization 150 is measured and stored for later reference, using any of the methods described above in conjunction with FIGS. 3 and 4 for measurement and storage of interval values.

The value of the pacemaker's A-V escape interval is gradually decremented until ventricular pacing pulses are delivered at the expirations of the A-V escape intervals. Thereafter the morphology of the paced R-waves is monitored to determine when it assumes the morphology of the R-wave following the initial ventricular pacing pulse 146. Comparison of waveform morphology may be as simple as optical observation of a video display by the physician or comparison of printouts of the electrogram made by printer 118, followed by a keyboard entry to inform the processor 114 of the specific A-V escape interval determined to be the maximum interval resulting in complete ventricular capture. Alternatively, if a light pen is provided, the physician may indicate the specific desired A-V escape interval by means of the light pen. In more elaborate embodiments selection of the maximum A-V interval providing complete ventricular capture may be performed automatically by the programmer apparatus if provided with digital signal processing circuitry.

As illustrated the ventricular pacing pulse 154 is followed by an R-wave having a waveform generally resembling a spontaneous R-wave (e.g., 150), indicating that complete ventricular capture has not occurred. The pacemaker's A-V escape interval continues to be decremented, with the waveforms of paced ventricular depolarizations monitored as described previously, until a ventricular pacing pulse is followed by a depolarization waveform corresponding to the waveform following the initial delivered ventricular pacing pulse 146. As illustrated, the depolarization waveform following ventricular pacing pulse 158 corresponds to the morphology of the depolarization waveform following pacing pulse 146. It is assumed that the escape interval $SAV_n$ following atrial pacing pulse 156 is the longest A-V escape interval which provides the required complete ventricular capture. The value of $SAV_n$ is then subtracted by the processor 114 from the intrinsic conduction time following sensed atrial depolarizations, to provide the ventricular sense offset (VSO). The value employed to represent the intrinsic A-V conduction time following sensed atrial depolarizations may be the value AVC derived as described in conjunction with FIG. 3 above, provided that the patient's sinus rate at that time generally corresponds to the patient's sinus rate during the measurement sequence described in conjunction with FIG. 5. Alternatively, measured times between sensed atrial depolarizations and sensed ventricular depolarizations during the measuring procedure illustrated in FIG. 5 may be averaged or otherwise employed to derive a value indicative of A-V conduction time. In either case, the derived value indicative of intrinsic A-V conduction time is compared to the duration of the longest pacemaker escape interval ($SAV_n$) which provides complete ventricular capture, and the difference between these two values is employed as the ventricular sense offset interval.

$SAV_n$ may be employed as the initial programmed duration for the pacemaker's A-V escape interval SAV following sensed atrial depolarizations, if desired, as it corresponds to the initial value of AVC minus VSO. The initial duration of PAV may correspondingly be $SAV_n$ plus ASO, corresponding to AVC minus VSO plus ASO. Alternatively, a relatively long preset A-V interval (e.g. 300 ms) duration may be employed, allowing the pacemaker to immediately update the values of its A-V escape intervals after implant, as described below in conjunction with FIGS. 6 and 7.

FIG. 5 illustrates the determination of the value of VSO in the presence of a spontaneous atrial rate high enough to inhibit atrial pacing. However, the procedure may correspondingly be performed by varying A-V escape interval durations following atrial pacing pulses, if the patient's spontaneous atrial rate is too low. In such case, the value of VSO will be calculated by subtracting the value of the longest pacemaker escape interval ($PAV_n$) which provides complete ventricular capture from the measured conduction time following atrial pacing pulses (PAVC), derived as discussed above in conjunction with FIG. 4. In this case, $PAV_n$ may correspondingly serve as the initial value of PAV, with the initial value of SAV set to $PAV_n$ minus ASO.

Figure 6:
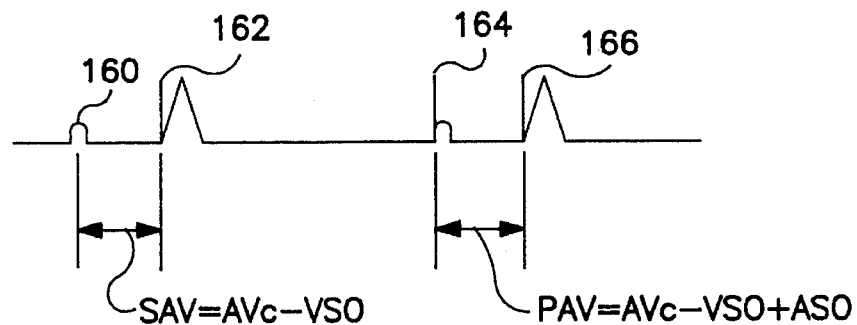
FIG. 6 is a simulated ECG strip illustrating the calculation of the SAV and PAV escape intervals according to the preferred embodiment of the present invention.

FIG. 6 illustrates calculation of subsequent base A-V escape intervals by the implanted pacemaker. The A-V escape interval SAV between sensed atrial depolarization 160 and a delivered ventricular pacing pulse 162 is defined to be equal to AVC minus VSO, while the escape interval PAV separating delivery of an atrial pacing pulse 164 and delivery of a ventricular pacing pulse 168 is set equal to AVC minus VSO, plus ASO, with the result that PAV correspondingly equals SAV plus ASO, as discussed above. During operation of the pacemaker, updating of the pacemaker's A-V escape intervals is accomplished by updating AVC. Two methods of updating the value of AVC are illustrated in FIGS. 7 and 8.

Figure 7:
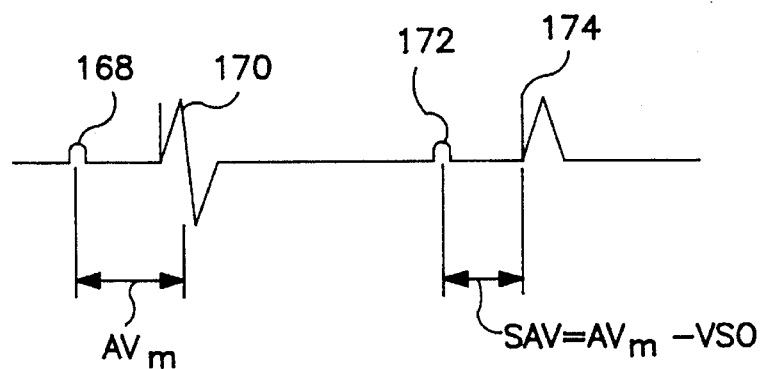
FIG. 7 is a simulated ECG strip illustrating the updating of the value of the pacemaker's A-V escape intervals in response to sensing of a ventricular depolarization during a preceding A-V escape interval.

FIG. 7 is a simulated electrocardiogram illustrating a first method by which the pacemaker updates the stored value of AVC, for use in defining the durations of the A-V escape intervals SAV and PAV. Following a sensed atrial depolarization 168, a ventricular depolarization 170 is sensed. The pacemaker measures the duration $AV_m$ separating the two sensed events and stores it. $AV_m$ is designated as the new value of AVC, and thus following the next subsequent sensed atrial depolarization 172, a new escape interval SAV is initiated, equal to the new value of AVC, minus VSO. PAV is correspondingly updated.

Figure 8:
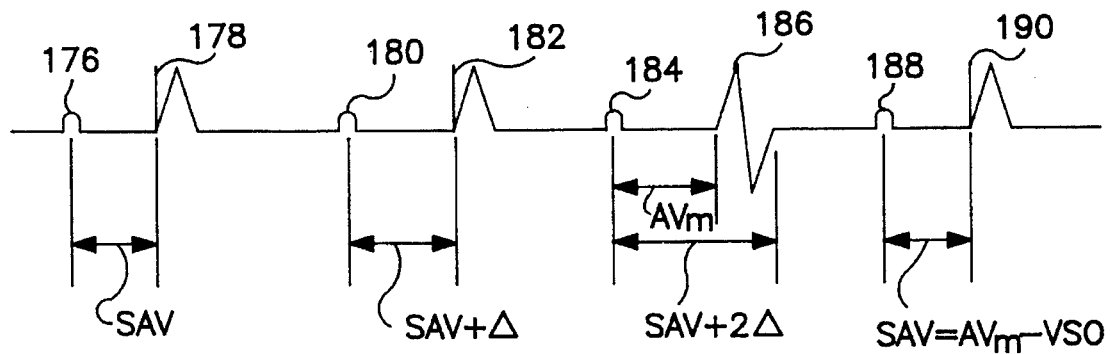
FIG. 8 illustrates the method for updating the pacemaker's A-V escape intervals in response to delivery of a prolonged sequence of atrial synchronized ventricular pacing pulses, according to the present invention.

FIG. 8 illustrates a mechanism for adjusting the value of AVC, in situations where extended series of atrial synchronized ventricular pacing pulses have been delivered, in order to determine whether the intrinsic A-V conduction time has lengthened, which would allow for longer pacemaker A-V escape intervals, while maintaining complete ventricular capture. At 176 an atrial depolarization is sensed, followed one A-V escape interval (SAV) later by a delivered ventricular pacing pulse 178. Ventricular pacing pulse 178, for example, may be the 60th successive atrial synchronized ventricular pacing pulse, which, in conjunction with a resting heart rate, triggers operation of the A-V escape interval scan for updating the value of AVC. Following the next atrial depolarization 180, a prolonged A-V escape interval (SAV+ Δ) is defined. As illustrated at the expiration of this escape interval, a ventricular pacing pulse is generated at 182. If, instead of a sensed atrial depolarization, an atrial pacing pulse had been delivered at 180, the corresponding timed pacemaker A-V escape interval would have been equal to PAV +Δ. Because no ventricular depolarization was sensed during the prolonged A-V escape interval ending with pacing pulse 182, on the next subsequent sensed atrial depolarization at 184, a new lengthened A-V escape interval, SAV plus 2Δ is defined. In this case, a ventricular depolarization 186 is sensed during the extended A-V escape interval, and the time interval $AV_m$ between sensed atrial depolarization 184 and sensed ventricular depolarization interval 186 is measured and stored. The value of AVC is then set equal to $AV_m$, and following the next sensed atrial depolarization at 188, a new pacemaker A-V escape interval SAV is defined equal to AVC ($AV_m$) minus VSO, extending until delivery of the ventricular pacing pulse at 190. PAV is correspondingly updated.

In the context of the present invention it should be understood that the available ranges for the values of the pacemaker's A-V escape intervals PAV and SAV are necessarily limited. Extension of the SAV and PAV intervals to values greater then 350 mill seconds, for example, may be prohibited. Thus, in the event that the A-V escape intervals are successively incremented during the scan until they exceed the available maximum A-V delay by an interval in excess of expected values for the ventricular sense offset, further extensions of the A-V escape interval are disabled and the A-V escape interval scan function is preferably disabled for a preset scan delay period, e.g., ten minutes or more, in order to prevent lack of ventricular sensing or lack of intrinsic atrial-ventricular conduction from triggering excessive numbers of A-V escape interval scans. Similarly, it is envisioned that minimum A-V escape intervals may be specified, e.g., 100–150 milliseconds, to prevent accomplishment of complete ventricular capture at the cost of comprising hemodynamics. As set forth in the above Jeanrenaud et al. article, if extremely short A-V escape intervals are required to accomplish complete ventricular capture, the patient may fail to benefit from the therapy. If such a patient is identified during initialization process, it is to be expected that the automated setting and updating of A-V escape intervals provided by the present invention to accomplish complete ventricular capture would not be employed. If the patient's condition changes after implant such that extremely short A-V intervals would be required in order to accomplish complete ventricular capture, the minimum available A-V escape interval period prevents excessive shortening of the A-V escape interval. On follow up, if the physician determines that the A-V interval has been shortened to the minimum available value, the physician may wish to test the patient to determine whether or not the shortened A-V escape intervals are continuing to provide any hemodynamic benefit. If not, the physician may wish to disable the feature entirely or to provide drug therapy to prolong intrinsic A-V conduction times.

Figure 9:
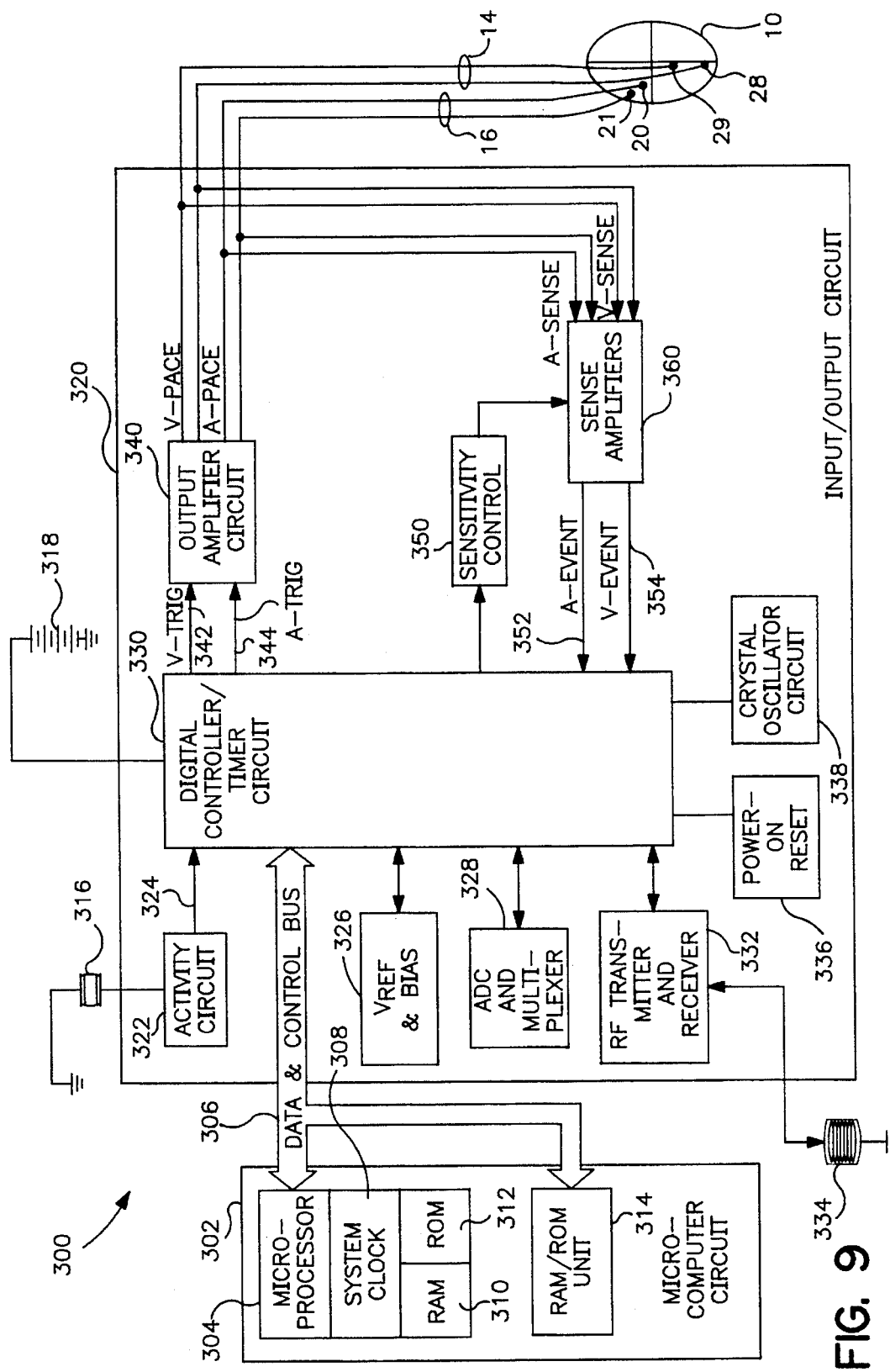
FIG. 9 is a block diagram of the dual chamber pacemaker illustrated in FIGS. 1 and 2, illustrating the functional components of the device in more detail.

FIG. 9 is a block functional diagram of the pacemaker illustrated in FIG. 1 and 2, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14 as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The output circuit 340 and sense amplifier circuit 360 may contain pulse generators and sense amplifiers corresponding to any of those presently employed in commercially marketed cardiac pacemaker. Control of timing and other functions within the pacemaker circuit is provided by digital controller/timer circuit 330, which includes a set of timers and associated logic. Digital controller/timer circuit defines the basic pacing interval of the device, which may take the form of an A-A escape interval initiated on atrial sensing or pacing and triggering atrial pacing at the expiration thereof or may take the form of a V-V escape interval, initiated on ventricular sensing or pacing and triggering ventricular pulse pacing at the expiration thereof. Digital controller/timer circuit 330 similarly defines the A-V escape intervals SAV and PAV, discussed above. The specific values of the intervals defined are controlled by the microcomputer circuit 302 by means of data and control bus 306. Sensed atrial depolarizations are communicated to the digital controller/timer circuit 330 on A event line 352, with ventricular depolarizations communicated to the digital controller/timer circuit 330 on V event line 354. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350.

In the embodiment illustrated in FIG. 9, the pacemaker is provided with a piezo electric sensor 316 which is intended to monitor patient activity, in order to allow provision of rate responsive pacing, such that the defined pacing rate (A-A escape interval or V-V escape interval) increases with increased demand for oxygenated blood. Sensor 316 generates electrical signals in response to sensed physical activity which are processed by activity circuit 322 and provided to digital controller/timer circuit 330. Activity circuit 322 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Similarly, the present invention may also be practiced in non-rate responsive pacemakers.

Transmission to and from the external programmer illustrated in FIG. 2 is accomplished by means of antenna 334 and associated RF transmitter and receiver 332, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include both the ability to transmit stored digital information as well as the ability to transmit electrocardiograms from either the atrium, or the ventricle, according to the teaching of the above-cited Wyborny patent, as well as transmission of Marker pulses indicating the occurrence of sensed and paced depolarizations in the atrium and ventricle, as disclosed in the cited Markowitz patent. In addition, in the context of the present invention, if intervals between sensed and paced events are measured internally within the pacemaker, these intervals may be encoded in digital form and transmitted via our transmitter 332 and antenna 334 to the external programmer for display and/or analysis as discussed above in conjunction with FIGS. 3–5, for purposes of performing the initialization procedure of the present invention.

Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage co provide real time telemetry if a cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Microcomputer circuit 302 controls the operational functions of digital controller/timer 324, specifying which timing intervals are employed, and controlling the duration of the various timing intervals, via data and control bus 306. Microcomputer circuitry contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every two seconds, may be provided in order to allow the microprocessor to analyze the output of the activity circuit 322 and update the basic rate interval (A-A or V-V) of the device. In addition, in a preferred embodiment of the invention, the microprocessor 304 may also serve to define variable A-V escape intervals and atrial and ventricular refractory periods which may also decrease in duration along with decreases in duration of the basic rate interval. For example, the microprocessor may specify a variable rate adaptive decrement interval (RAD) to be subtracted from the defined A-V escape intervals when the heart rate (paced or sensed) is above a defined resting or "start" rate. Similarly microprocessor 304 may define atrial and/or ventricular refractory periods which decrease in duration as a function of sensed or paced heart rate.

In the context of the present invention, microprocessor 304, in response to an interrupt indicating delivery of a ventricular pacing pulse or sensing of a ventricular depolarization, updates the value of AVC, if necessary, allowing for adjustment of the pacemaker's A-V escape intervals. Operation of the microprocessor to control the duration of the A-V escape intervals in conjunction with the present invention is illustrated in more detail in conjunction with the flowcharts of FIGS. 10 and 11.

The illustrated circuitry of FIG. 9 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a pacemaker having an architecture as illustrated in FIG. 9, and a circuit architecture as illustrated in FIG. 9 is not believed to be a prerequisite to enjoying the benefits of the present invention.

Figure 10:
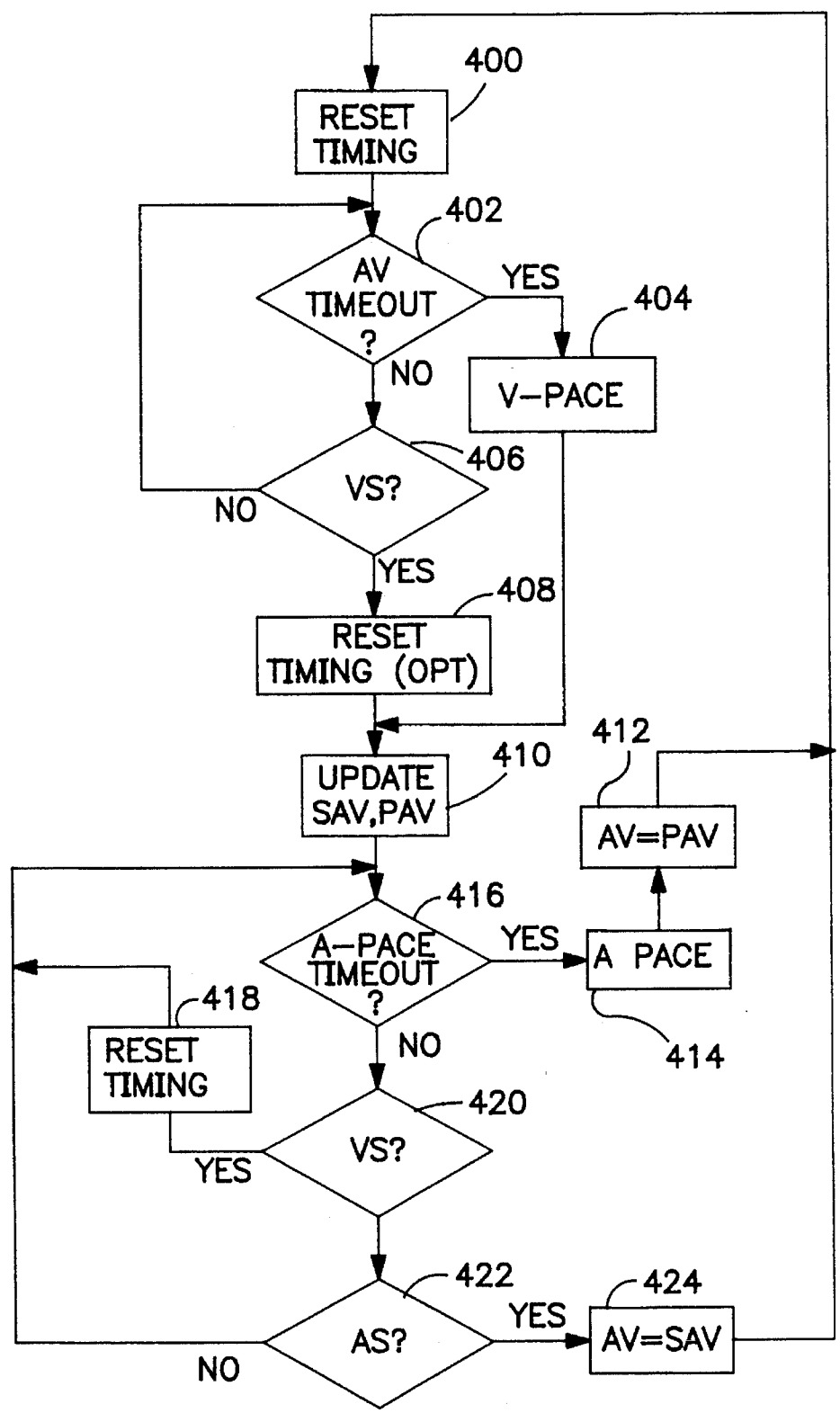
FIG. 10 is a functional flowchart illustrating the overall function of the pacemaker illustrated in FIG. 1, 2 and 9, operating in DDD pacing mode.

FIG. 10 is a functional flowchart of the operation of the device illustrated in FIGS. 1, 2 and 9, in DDD pacing mode. For the sake of simplicity, functional steps corresponding to the provision of refractory and blanking periods have been omitted, to allow for easier understanding of the overall operational mode. In the flowchart of FIG. 10, it is assumed that the basic timing of the device is based around of the definition of an atrial escape interval (A-A interval) which may be fixed or may vary as a result of the output of a physiologic sensor. This A-A interval is reset at 400, along with the current A-V escape intervals SAV and PAV. During the A-V escape interval the device awaits either time out of the current A-V escape interval (PAV or SAV) at 402 or ventricular sensing at 406. If ventricular sensing does not occur prior to A-V escape interval time out, a ventricular pacing pulse is generated at 404, and the values of the A-V escape intervals are updated, if necessary, at 410, according to the present invention. If a ventricular depolarization is sensed at 406, prior to expiration of the current A-V escape interval, the pacemaker's timing may optionally be reset at 408 to deliver an atrial pacing pulse at a V-A escape interval thereafter equal to the A-A escape interval minus the current A-V escape interval, or the device may proceed directly to updating the A-V escape intervals at 410, and not alter the timing of the next scheduled atrial pacing pulse at the expiration of the A-A escape interval.

Following update of the base A-V escape intervals at 410, the device awaits expiration of the A-A (or optionally the V-A) escape interval at 416, sensing of a ventricular depolarization at 420 outside of the ventricular refractory period, or sensing of an atrial depolarization at 422, outside of the atrial refractory period. If the A-A (or V-A) escape interval expires at 416 without preceding atrial or ventricular sensing, an atrial pacing pulse is generated at 414, and the next succeeding A-V escape interval is defined to be equal to PAV at 412, followed by reset of the A-A escape interval and the A-V escape interval at 400.

In the event that a ventricular depolarization is sensed at 420, prior to expiration of the A-A escape interval, the timing is reset to trigger atrial pacing at the expiration of a V-A interval (A-A interval minus PAV or SAV). In the context of the present invention, a ventricular depolarization sensed at this point is not effective to trigger an update of the SAV and PAV intervals. If an atrial depolarization is sensed at 422, prior to expiration of the A-A (or V-A) interval, the subsequent A-V escape interval is defined to be equal to SAV at 424, and the A-A and A-V escape intervals are reset at 400.

Figure 11:
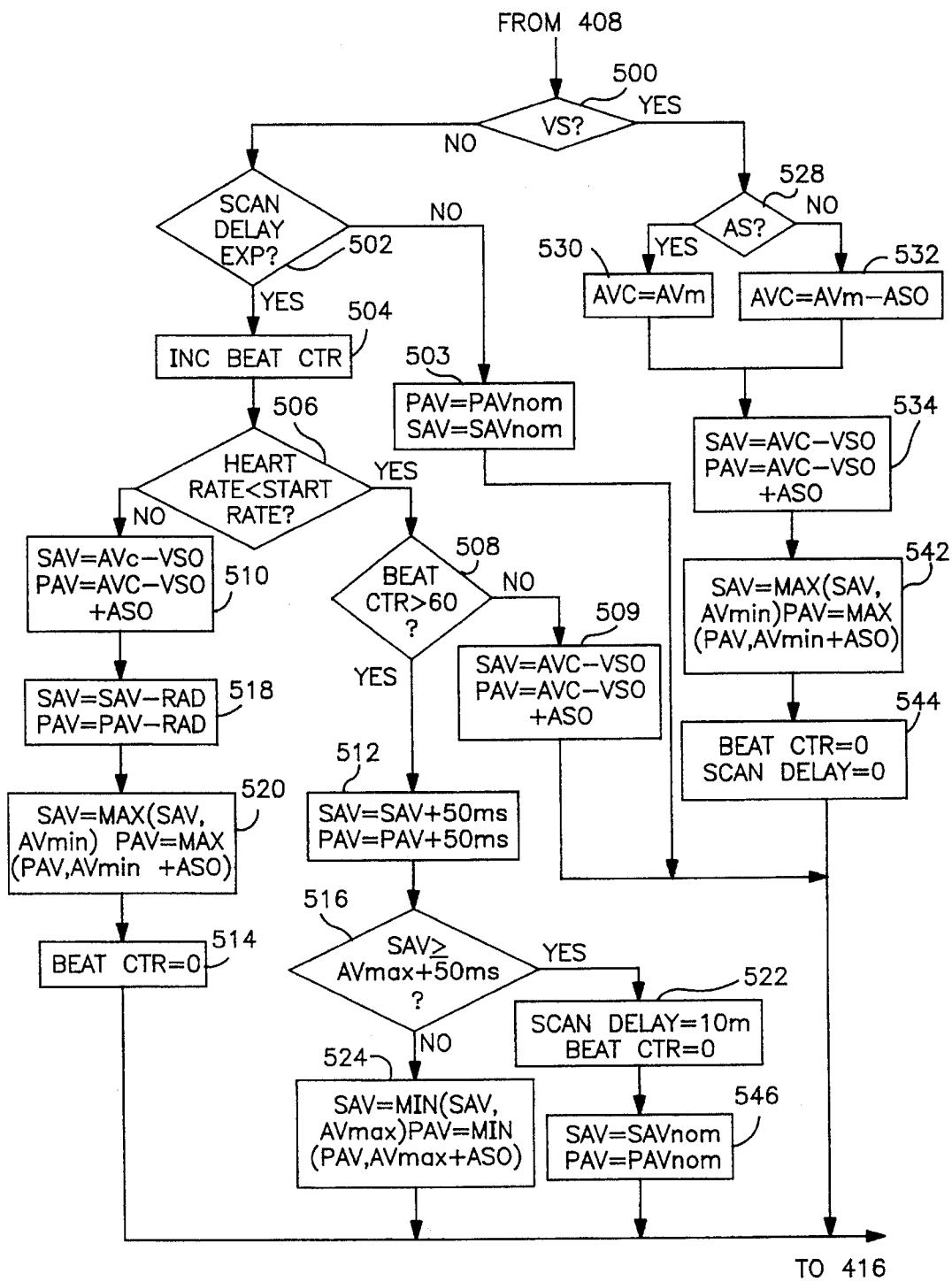
FIG. 11 is a flowchart illustrating the methods by which the pacemaker illustrated in FIGS. 1, 2 and 9 updates its A-V escape interval durations, as illustrated in FIGS. 7 and 8.

Functional block 410, which contains the step of updating the values of the SAV and PAV, intervals is illustrated in more detail in FIG. 11, and includes the two mechanisms for updating the value of the intrinsic conduction time, AVC, described above in conjunction with FIGS. 7 and 8. The flowchart of FIG. 11 is entered from 408, where the device determines at 500 whether the preceding ventricular event was a sensed depolarization or a delivered pacing pulse.

If ventricular event preceding decision step 500 was delivered pacing pulse, the device checks at 502 to determine whether the A-V interval scan delay has expired. This delay corresponds to the period during which the A-V scan function is disabled, as described in conjunction with FIG. 8, following an unsuccessful attempt to sense a ventricular depolarization while scanning through available and acceptable A-V intervals. If this delay has not expired, indicating that an unsuccessful scan of A-V escape intervals had recently been attempted, the device sets the values of SAV and SAV to preset nominal values at 503. The nominal values of SAV and PAV may be preset, e.g. 120–150 ms, or may be the last values of SAV and PAV prior to the onset of the A-V escape interval scan. The pacer then simply proceeds to block 416 of FIG. 10 to await expiration of the atrial escape interval.

In the event that the scan delay has expired, or was previously reset to zero, the beat counter is incremented at 504. The beat counter is a count of sequential atrial synchronized ventricular pacing pulses as described above in conjunction with FIG. 8. At 506, the device checks to determine whether the present heart rate is less than the defined resting or "start" rate. If the heart rate is not below the start rate, SAV is set equal to the previously defined A-V conduction time AVC, minus VSO and the value of PAV is set equal to AVC minus VSO plus ASO at 510. The current values of SAV and PAV are decremented by rate adaptive decrements (RAID) to provide shortened A-V escape intervals associated with the detected non-resting heart rate, as discussed above at 518. At 520, SAV and PAV are set equal to the greater of their durations as defined at 518 and corresponding minimum A-V escape interval durations. The beat counter is reset to zero at 514, so that a subsequent attempt to scan A-V escape intervals will be delayed for a predetermined number (e.g. 60) paced ventricular beats.

In the event that the heart rate is below the defined resting or start heart rate at 506, the pacer checks at 508 to determine whether the beat counter is greater than or equal to a predetermined number, e.g., 60, of sequential atrial synchronized ventricular pacing pulses. If not, the value of SAV is set equal to the previously determined value of AVC minus VSO, and PAV is set equal to the previously determined value of AVC minus VSO, plus ASO at 509. If, however, the beat counter is at or greater than the predetermined number of beats at 508, the values of SAV and PAV are incremented at 512 by a predetermined increment Δ, for example 50 milliseconds. At 516 the device checks to determine whether the incremented value of SAV exceeds the maximum acceptable value for SAV by more than a predetermined amount, e.g., 50 milliseconds. If so, this would indicate that the A-V scan has extended the A-V escape intervals to a degree where expected ventricular sense offset values would not allow for permitted A-V escape intervals providing complete ventricular capture. In other words, the scan has been unsuccessful in locating a new, acceptable value for the intrinsic A-V conduction time AVC. Under these circumstances, the delay time for disabling subsequent A-V interval scans is set equal to a predetermined period of time, e.g., ten minutes at 522, and the beat counter is reset to zero. The values of SAV and PAV are set to nominal values at 546, which may either be preset values as discussed above or may be the last values of SAV and PAV prior to the unsuccessful A-V interval scan.

If, however, the value of the extended SAV is appropriate at 516, the device checks at 524 to determine whether the newly calculated values of SAV and PAV are less than or equal to their corresponding allowed maximum values, and if not, sets the values of SAV and PAV equal to their corresponding maximum allowed values. The device then returns to block 416, to await time out of the A-A escape interval.

Sequential extensions of the A-V escape intervals as defined by the pacemaker continue until either the A-V escape interval scan is determined to be unsuccessful at 516 or until a ventricular depolarization is sensed during an extended A-V escape interval, allowing substitution of a new value for AVC and updating of the values of SAV and PAV, according to the present invention.

In the event that the ventricular event prior to decision point 500 was a sensed ventricular depolarization, the device checks at 528 to determine whether the atrial event which initiated timing of the A-V escape interval in progress was a sensed atrial depolarization or a delivered atrial pacing pulse. The device may check to determine this by simply checking whether the SAV or PAV escape interval was being timed when the ventricular depolarization was sensed. In the event that the SAV interval was being timed, the new value of the A-V conduction time AVC is set equal to the measured time between atrial sensing and ventricular sensing at 530. This time interval may be determined simply by recording the time at which the ventricular sensing occurred, which will be reflected by the corresponding count in the timer within the pacemaker timing and control circuitry responsible for determining the A-V escape interval then in progress. In the event that the previous A-V escape interval was initiated in response to atrial pacing, the new value of the intrinsic A-V conduction time AVC is set equal to the measured A-V interval minus ASO at 532, so that the value of AVC corresponds to the expected time of conduction between a sensed atrial depolarization and sensed ventricular depolarization. At 534, SAV is set equal to AVC minus VSO and PAV is set equal to AVC minus VSO plus ASO. At 542, SAV and PAV are set equal to the greater of their durations as defined at 538 or 540 and corresponding minimum A-V escape interval durations. At 544, the delay timer is reset to zero and the beat counter is similarly reset to zero, indicating the occurrence of a sensed depolarization. The device then awaits atrial escape time out at 416, ventricular sensing at 420 or atrial sensing at 422 as described above in conjunction with FIG. 10.

The above specification discloses a device which operates in DDD or DDDR mode, which is the expected mode of operation of a pacemaker employing the present invention. However, it is envisioned that in certain patients, devices which operate in other dual chamber pacing modes such as VDD, VDDR, DVI or DVIR modes may also be appropriate. For example, in the case of a patient who suffers from a profound sinus bradycardia, a device operating in DVIR mode might provide the benefit of the present invention. Similarly, in a patient having an intact and fully functioning sinus node, and good atrial sensing by the pacemaker, a device operating in VDD mode might provide the benefit of the present invention. As such, it should be understood that the invention is believed to be of value in the context of any pacemaker which provides ventricular pacing pulses synchronized to either sensed atrial depolarizations or paced atrial depolarizations, and which has the ability to sense spontaneous ventricular depolarizations.

In conjunction with the above specification,

We claim:

1. A method of pacing a heart, comprising:
   detecting atrial and ventricular depolarizations:

measuring atrial—ventricular conduction time of said heart;

delivering ventricular pacing pulses capable of completely capturing said heart's ventricles absent concurrent spontaneous depolarizations of said ventricles;

determining a time interval following an atrial depolarization of said heart, such that a ventricular pacing pulse delivered at expiration of said time interval results in complete ventricular capture of said heart;

deriving a first offset interval based on relative durations of said determined time interval and said measured atrial—ventricular conduction time;

defining A-V escape intervals following atrial depolarizations;

delivering ventricular pacing pulses at the expirations of said A-V escape intervals absent ventricular depolarizations during said A-V escape intervals;

measuring atrial—ventricular conduction time of a ventricular depolarization occurring within a said A-V escape interval; and defining duration of a subsequent said A-V escape interval based on said first offset interval and said atrial—ventricular conduction time measured within said A-V escape interval.

2. A method of pacing a heart, comprising:

detecting atrial and ventricular depolarizations:

measuring atrial—ventricular conduction time of said heart;

delivering ventricular pacing pulses capable of completely capturing said heart's ventricles absent concurrent spontaneous depolarizations of said ventricles;

determining a time interval following an atrial depolarization of said heart, such that a ventricular pacing pulse delivered at expiration of said time interval results in complete ventricular capture of said heart;

deriving a first offset interval based on relative durations of said determined time interval and said measured atrial—ventricular conduction time;

defining an A-V escape intervals following atrial depolarizations;

delivering ventricular pacing pulses at the expirations of said A-V escape intervals absent ventricular depolarizations during said A-V escape intervals;

extending durations of said A-V escape intervals until a ventricular depolarization falls within a said extended A-V escape interval;

measuring atrial—ventricular conduction time of a ventricular depolarization occurring within a said extended A-V escape interval; and defining duration of a subsequent said A-V escape interval based on said first offset interval and said atrial—ventricular conduction time measured within said extended A-V escape interval.

3. A method according to claim 2, further comprising the step of counting sequentially delivered ventricular pacing pulses and wherein said extending step comprises extending said A-V escape intervals in response to counting a predetermined number of sequentially delivered ventricular pacing pulses.

4. A method according to claim 2, wherein said extending step comprises extending said A-V escape intervals up to a predefined maximum A-V escape interval, and further comprising the step of preventing subsequent extensions of said A-V escape intervals for a period of time in response to failure of a ventricular depolarization to occur within said maximum A-V escape interval.

5. A method of pacing a heart, comprising:

sensing atrial depolarizations:

delivering a ventricular pacing pulse to said heart to induce complete ventricular capture; "determining a ventricular depolarization waveform caused by said ventricular pacing pulse and indicative of complete ventricular capture;"

defining A-V escape intervals following atrial depolarizations;

delivering ventricular pacing pulses at expirations of said A-V escape intervals;

varying durations of said A-V intervals while monitoring waveforms of ventricular depolarizations following said ventricular pacing pulses to define an A-V escape interval such that a ventricular pacing pulse delivered at expiration of said defined A-V escape interval results in complete ventricular capture of said heart; and employing said defined A-V escape interval to control durations of subsequent A-V escape intervals.

6. A method according to claim 5, wherein said employing step comprises employing said defined A-V escape interval as subsequent A-V escape intervals.

7. A method according to claim 5, further comprising the step of measuring atrial—ventricular conduction time of said heart, and wherein said employing step comprises the steps of:

deriving a first offset interval based on relative durations of said defined A-V escape interval and said measured atrial—ventricular conduction time;

measuring atrial—ventricular conduction time of a ventricular depolarization occurring within a first one of said subsequent A-V escape intervals; and defining duration of a second, later one of said subsequent A-V escape intervals based on said first offset interval and said atrial—ventricular conduction time measured within first one of said subsequent A-V escape intervals.

8. A method according to claim 1 or claim 2, further comprising the steps of sensing spontaneous atrial depolarizations and delivering atrial pacing pulses and wherein said step of defining duration of a subsequent A-V escape interval comprises defining a first A-V escape interval duration to be employed following spontaneous atrial depolarizations and a second A-V escape interval to be employed following delivered atrial pacing pulses.

9. A method according to claim 1 or claim 2, wherein said step of defining duration of a subsequent A-V escape interval comprises determining heart rate and defining duration of a subsequent said A-V escape interval based on said first offset interval, said atrial—ventricular conduction time measured within said extended A-V escape interval, and said determined heart rate.

10. Apparatus for pacing a heart, comprising:

means for sensing atrial depolarizations;

means for defining a first offset interval;

means for defining A-V escape intervals following atrial depolarizations;

means for sensing ventricular depolarizations of said heart;

means for delivering ventricular pacing pulses at the expirations of said A-V escape intervals in the absence of ventricular depolarizations during said A-V escape intervals;

means for extending durations of said A-V escape intervals until a ventricular depolarization falls within a said extended A-V escape interval;

means for measuring atrial—ventricular conduction time of a sensed ventricular depolarization occurring within a said extended A-V escape interval; and means for defining duration of a subsequent said A-V escape interval by subtracting said first offset interval and said atrial—ventricular conduction time measured within said extended A-V escape intervail;

wherein said means for extending said A-V escape intervals comprises means for extending said A-V escape intervals up to a predefined maximum A-V escape interval, and further comprises means for preventing subsequent extensions of said A-V escape intervals for a period of time in response to failure of a ventricular depolarization to occur within said maximum A-V escape interval.

11. A apparatus according to claim 10, further comprising means for counting sequentially delivered ventricular pacing pulses and wherein said means for extending said A-V escape intervals comprises extending said A-V escape intervals in response to counting a predetermined number of sequentially delivered ventricular pacing pulses.

12. Apparatus according to claim 10, wherein said means for extending said A-V escape intervals comprises means for extending said A-V escape intervals up to a predefined maximum A-V escape interval, and further comprises means for preventing subsequent extensions of said A-V escape intervals for a period of time in response to failure of a ventricular depolarization to occur within said maximum A-V escape interval.

13. Apparatus according to claim 10, further comprising means for delivering atrial pacing pulses and wherein said means for defining duration of a subsequent A-V escape interval comprises means for defining a first A-V escape interval duration to be employed following a sensed spontaneous atrial depolarizations and means for defining a second A-V escape interval to be employed following delivered atrial pacing pulses.

14. Apparatus according to claim 10, wherein said means for defining duration of a subsequent A-V escape interval comprises means for determining heart rate and means for defining duration of a subsequent said A-V escape interval based on said first offset interval, said atrial—ventricular conduction time measured within said extended A-V escape interval, and said determined heart rate.

15. Apparatus for pacing a heart, comprising:

means for sensing atrial and ventricular depolarizations:

means for measuring atrial—ventricular conduction time of said heart;

means for delivering ventricular pacing pulses capable of completely capturing said heart's ventricles absent concurrent spontaneous depolarizations of said ventricles;

means for determining a time interval following an atrial depolarization of said heart, such that a said ventricular pacing pulse delivered at expiration of said time interval results in complete ventricular capture of said heart;

means for deriving a first offset interval based on relative durations of said determined time interval and said measured atrial—ventricular conduction time;

means for defining A-V escape intervals following atrial depolarizations;

means for sensing ventricular depolarizations of said heart;

means for delivering ventricular pacing pulses at the expirations of said A-V escape intervals absent sensed ventricular depolarizations during said A-V escape intervals;

means for measuring atrial—ventricular conduction time of a ventricular depolarization occurring within a said A-V escape interval; and means for defining duration of a subsequent said A-V escape interval based on said first offset interval and said atrial—ventricular conduction time measured within said A-V escape interval.

16. Apparatus for pacing a heart, comprising:

means for sensing atrial and ventricular depolarizations:

means for measuring atrial—ventricular conduction time of said heart;

means for delivering ventricular pacing pulses capable of completely capturing said heart's ventricles absent concurrent spontaneous depolarizations of said ventricles;

means for determining a time interval following an atrial depolarization of said heart, such that a ventricular pacing pulse delivered at expiration of said time interval results in complete ventricular capture of said heart;

means for deriving a first offset interval based on relative durations of said determined time interval and said measured atrial—ventricular conduction time;

means for defining an A-V escape intervals following atrial depolarizations;

means for sensing ventricular depolarizations of said heart;

means for delivering ventricular pacing pulses at the expirations of said A-V escape intervals absent ventricular depolarizations during said A-V escape intervals;

means for extending durations of said A-V escape intervals until a sensed ventricular depolarization falls within a said extended A-V escape interval;

means for measuring atrial—ventricular conduction time of a sensed ventricular depolarization occurring within a said extended A-V escape interval; and means for defining duration of a subsequent said A-V escape interval based on said first offset interval and said atrial—ventricular conduction time measured within said extended A-V escape interval.

17. Apparatus for pacing a heart, comprising:

means for sensing atrial and ventricular depolarizations:

means for delivering a ventricular pacing pulse to said heart to induce complete ventricular capture;

means for delivering ventricular pacing pulses capable of completely capturing said heart's ventricles absent concurrent spontaneous depolarizations of said ventricles;

means for monitoring waveforms of ventricular depolarizations:

means for determining a ventricular depolarization waveform indicative of complete ventricular capture;

means for defining A-V escape intervals following atrial depolarizations;

means for delivering said ventricular pacing pulses at expirations of said A-V escape intervals;

means for varying durations of said A-V intervals while monitoring waveforms of ventricular depolarizations following said ventricular pacing pulses;

means responsive to said monitoring means, for identifying a said A-V escape interval duration such that a ventricular pacing pulse delivered at expiration of said identified A-V escape interval duration results in complete ventricular capture of said heart; and means for employing said identified A-V escape interval duration to define durations of subsequent said A-V escape intervals.

18. Apparatus according to claim 17, wherein said employing means comprises means for employing said identified A-V escape interval duration as a subsequent said A-V escape intervals.

19. Apparatus according to claim 17, further means for measuring atrial—ventricular conduction time of said heart, and wherein said employing means comprises:

means for deriving a first offset interval based on relative durations of said identified A-V escape interval and said measured atrial—ventricular conduction time;

means for measuring atrial—ventricular conduction time of a ventricular depolarization occurring within a first one of said subsequent A-V escape intervals; and means for defining duration of a second, later one of said subsequent A-V escape intervals based on said first offset interval and said atrial—ventricular conduction time measured within first one of said subsequent A-V escape intervals.

\* \* \* \* \*